(12) United States Patent
Nakamura

(10) Patent No.: US 8,911,394 B2
(45) Date of Patent: Dec. 16, 2014

(54) GAS MIST PRESSURE BATH DEVICE

(75) Inventor: Shoichi Nakamura, Higashichikuma-gun (JP)

(73) Assignees: Shoich Nakamura, Higashichikuma-Gun, Nagano (JP); ACP Japan Co., Ltd., Tokyo (JP)

( * ) Notice: Subject to any disclaimer, the term of this patent is extended or adjusted under 35 U.S.C. 154(b) by 410 days.

(21) Appl. No.: 12/735,286

(22) PCT Filed: Jun. 26, 2009

(86) PCT No.: PCT/JP2009/061719
§ 371 (c)(1),
(2), (4) Date: Jun. 29, 2010

(87) PCT Pub. No.: WO2009/157539
PCT Pub. Date: Dec. 30, 2009

(65) Prior Publication Data
US 2010/0286595 A1 Nov. 11, 2010

(30) Foreign Application Priority Data
Jun. 27, 2008 (JP) .................................. 2008-168231

(51) Int. Cl.
*A61M 37/00* (2006.01)
*A61K 33/00* (2006.01)
*A61H 33/14* (2006.01)
*A61H 33/00* (2006.01)

(52) U.S. Cl.
CPC ............... *A61K 33/00* (2013.01); *A61H 33/14* (2013.01); *A61H 33/60* (2013.01); *A61H 2201/165* (2013.01); *A61H 2205/065* (2013.01); *A61H 2033/143* (2013.01); *A61H 2033/145* (2013.01); *A61H 2201/1635* (2013.01)
USPC .............................................. 604/23; 604/24

(58) Field of Classification Search
USPC ........... 604/23, 24, 25, 26; 607/83, 84, 86, 91
See application file for complete search history.

(56) References Cited

U.S. PATENT DOCUMENTS 5,312,385 A * 5/1994 Greco ............................ 604/356
7,276,051 B1 * 10/2007 Henley et al. .................. 604/304

(Continued)

FOREIGN PATENT DOCUMENTS

| JP | 07-171189 | * | 7/1995 | ............. A61H 33/14 |
| JP | H07-171189 | | 7/1995 | |
| JP | 2005-205163 | | 8/2005 | |
| JP | 2007-181720 | * | 7/2007 | ............. A61H 33/14 |
| JP | 2007-252871 | | 10/2007 | |

(Continued)

*Primary Examiner* — Aarti B Berdichevsky
*Assistant Examiner* — Laura Schell
(74) *Attorney, Agent, or Firm* — Manabu Kanesaka

(57) ABSTRACT

The invention is to provide a gas mist pressure bath device which enables to cause efficiently absorb a gas mist into a skin or mucous membrane of a living-body, and attains to be compact and to lower cost. The device 10 is to cause oxygen, carbon dioxide, or a mixed gas (called as "gas" hereafter) of oxygen and carbon dioxide at a density of not less than a predetermined value to contact the skin or mucous membrane of the living-body, and the device comprises a gas mist generating means 11 for generating and supplying a mist (called as "gas mist" hereafter) prepared by pulverizing and dissolving the gas and liquid, and a substantially bag shaped living-body cover member 21 for covering the living-body's skin or mucous membrane and sealing inside, and the gas mist is supplied into the living-body cover member in order to heighten internal pressure therein so that the gas mist is caused to contact the living-body's skin or mucous membrane at a pressure more than the predetermined value.

15 Claims, 3 Drawing Sheets

(56) References Cited

U.S. PATENT DOCUMENTS

2006/0241549 A1* 10/2006 Sunnen .................. 604/23
2009/0143720 A1* 6/2009 Hovorka ................ 604/23

FOREIGN PATENT DOCUMENTS

| JP | U 3150689 | 4/2009 |
| WO | WO 2004/002393 | 1/2004 |

* cited by examiner

GAS MIST PRESSURE BATH DEVICE

RELATED APPLICATIONS

The present application is National Phase of International Application No. PCT/JP2009/061719 filed Jun. 26, 2009, and claims priority from, Japanese Application No. 2008-168231 filed Jun. 27, 2008, the disclosure of which is hereby incorporated by reference herein in its entirety.

TECHNICAL FIELD

The present invention relates a gas mist pressure bath device, in which a gas mist is prepared by pulverizing and dissolving carbon dioxide, oxygen or a mixed gas of carbon dioxide and oxygen, and a liquid, and the thus prepared gas mist is directly contacted to a skin or mucous membrane of a living-body for improving a blood circulation of the living-body.

BACKGROUND ART

It has conventionally been known that carbon dioxide (carbonic acid anhydride: $CO_2$, called as "carbon dioxide" hereafter) has both properties of being not only soluble in water (water-soluble) but also soluble in fat (fat-soluble) and if, therefore, only contacting the skin or mucous membrane of the living-body being as mixed with water and fat, carbon dioxide penetrates under a subcutaneous layer and expands blood vessels around penetrated carbon dioxide, and it works to improve a blood circulation. Owing to this action of accelerating the blood circulation, it displays various physiological effects such as dropping of blood pressure, improving of metabolism or accelerating to remove pain substance or waste product. Further, it has also anti-inflammation and anti-bacterial. Therefore, carbon dioxide has recently been given attention also from viewpoints of improving health or beauty other than the purpose of medical cares.

Carbon dioxide in the tissue of the living-body works to release oxygen carried in combination with hemoglobin in a red blood cell. Around parts at a high density of carbon dioxide, the red blood cell releases more oxygen. Thus, supply of oxygen to cells by the red blood cell is mainly controlled by carbon dioxide. In short, being without carbon dioxide, hemoglobin remains as combined with oxygen and the cell becomes unable to receive oxygen. As is seen, carbon dioxide is seen as a waste product resulted from action of oxygen, however, it plays in fact very important roles in the human living-body.

Further, in recent times, oxygen of high density has also widely been known as effective in activity of metabolism, fatigue recovery, stability of blood pressure and others.

As techniques of causing the living-body to absorb carbon dioxide at the comparatively narrow limited parts thereof, there have been disclosed as following.

(1) A device, which attaches a closing simple cover to the limited part of a human body and introduces carbon dioxide into the cover for carrying out the carbon dioxide bath (refer to, for example, Patent Document 1).

(2) A device, which inserts the limited part of the human body into the closing container (otherwise, attaching the container to the limited part of the human body) and introduces carbon dioxide into the container for carrying out the carbon dioxide bath (refer to, for example, Patent Document 2).

(3) A device, which attaches to the limited part of the human body a sealing and surrounding material composed of a container having an opening such as a bag body or a tubular body, seals an absorbing assistant material of helping skin-passing absorption of carbon dioxide in order to close the interior of the sealing and surrounding material, and introducing carbon dioxide thereinto for carrying out the carbon dioxide bath by (refer to, for example, Patent Document 3).

There have been proposed by present inventors the carbon dioxide pressure bath devices which are furnished with at least gas mist generating means, pressurizing means, and coating members of one or two layer structures for covering the skin or mucous membrane of the living-body and for causing carbon dioxide to contact the skin or mucous membrane at pressure more than a predetermined value.

CITATION LIST

Patent Documents

Patent Document 1: Patent Laid-Open No. 07-171189
Patent Document 2: Patent Laid-Open No. 2007-252871
Patent Document 3: Domestic Re-publication WO2004/002393

SUMMARY OF INVENTION

Problems to be Solved by the Invention

However, in the devices for the prior art carbon dioxide bath described in the above mentioned patent documents 1 to 3, such problems were involved that the capacities of the container, cover or bag enclosing carbon dioxide were large, and if being wholly filled, a large quantity of carbon dioxide was consumed. But for putting the devices to practical use, it is inevitable to leave margins, to some extent, to the container, cover or bag in order to cope with users' various body figures. Making the enclosing space of carbon dioxide compact was difficult, and as a result, suppression of consuming amount of carbon dioxide was troublesome.

On the other hand, in the carbon dioxide pressure bath devices having already been proposed by the present inventors, it is possible to largely heighten an absorption rate of carbon dioxide into the skin or mucous membrane by causing carbon dioxide to contact the skin or mucous membrane at values higher than a predetermined pressure value by a pressure means, while a device like a compressor as the pressurizing means is necessary. Therefore, increase of cost is invited, while the device is large scaled, so that it is unsuitable to ordinary uses as in home. Further, the coating part has the complicated structure, so that a production cost rises.

Besides, there has not been present up to now a device which can absorb by skin-passing at efficiently not only carbon dioxide but oxygen and a mixed gas of carbon dioxide and oxygen.

In view of the above mentioned problems, it is an object of the invention to provide a gas mist pressure bath device which is possible to efficiently absorb even the gas of a small amount through the skin or mucous membrane of the human living-body, and can be made compact and reduce cost.

Means for Solving the Problem

For accomplishing the object, the invention is concerned with the device for causing oxygen, carbon dioxide, or a mixed gas (called as "gas" hereafter) of oxygen and carbon dioxide at a density of not less than a predetermined value to contact the skin or mucous membrane of the living-body, and this device comprises a gas mist generating means for generating and supplying a mist (called as "gas mist" hereafter)

prepared by pulverizing and dissolving the gas and liquid, and a substantially bag shaped living-body cover member for covering the living-body's skin or mucous membrane and sealing inside thereof the gas mist from the gas mist generating means, and is characterized in that the gas mist is supplied into the living-body cover member in order to heighten internal pressure therein so that the gas mist is caused to contact the living-body's skin or mucous membrane at pressure more than the predetermined value.

By the way, the invention refers it as "pulverizing and dissolving" to pulverize liquid into fine liquid drops, and cause to contact the gas (carbon dioxide, oxygen, or a mixed gas of carbon dioxide and oxygen).

Herein, preferably, the living-body cover member is furnished with reinforcing means for strengthening it. The living-body cover member is furnished, at its opening portion, with fastening means fabricated with one or plural combination of a rubber, string or face fastener, thereby to avoid the gas mist from running away into air atmosphere. Preferably, there is provided one or plural adhesive means having viscosity to the living-body's skin or mucous membrane on the face of the living-body cover member contacting the skin or mucous membrane.

In regard to the above mentioned liquid, suitable are water, ionic water, physiological salt solution, anti-allergic agent, anti-inflammatory agent, anti-febrile, anti-fungus agent, or anti-influenza virus. Otherwise, the above liquid is water containing one or plural medicines of menthol, vitamin E, vitamin C derivative, retinol, anesthetic, cyclodextrin, complex of photocatalyst and apatite, hyaluronic acid, coenzyme Q10, seed oil, propolith, or high density carbonate spring, ionic water, physiological salt solution, anti-allergic agent, anti-inflammatory agent, anti-febrile, anti-fungus agent, or anti-influenza virus.

Grain sizes of the gas mist supplied from the gas mist generating means to the living-body cover member are suitably not more than 10 μm.

In addition, optimum pressing by the pressing means of the living-body cover member is 1.02 to 2.5 air pressure.

It is preferable that the living-body cover member has a gas mist supply opening for introducing the gas mist supplied from the gas mist generating means into the living-body cover member, and this gas mist supply opening is provided therein with the check valve.

Desirably, the gas mist generating means has a gas mist supply pipe for supplying the gas mist into the living-body cover member, and this gas mist supply pipe has a filter for removing liquid drops attached to a pipe inside. Further, a whole or one of the gas mist supply pipe is suitably composed of a cornice shaped pipe, and this gas mist supply pipe is provided with the check valve.

Advantageous Effect of the Invention

According to the gas mist pressure bath device of the invention, since the living-body cover member for carrying out the gas mist pressure bath is composed of an elastic member, the interior of the living-body cover member can be pressurized by only sending the gas mist. Thereby, another pressurizing means is not further requested and the device can be made compact. Since any especial actuation is not necessary, highly effective and easy gas mist pressure bath may be performed by only sending the gas mist into the living-body cover member.

DESCRIPTION OF EMBODIMENTS

In the following description, explanations will be made to embodiments of this invention, referring to the attached drawings.

Figure 1:
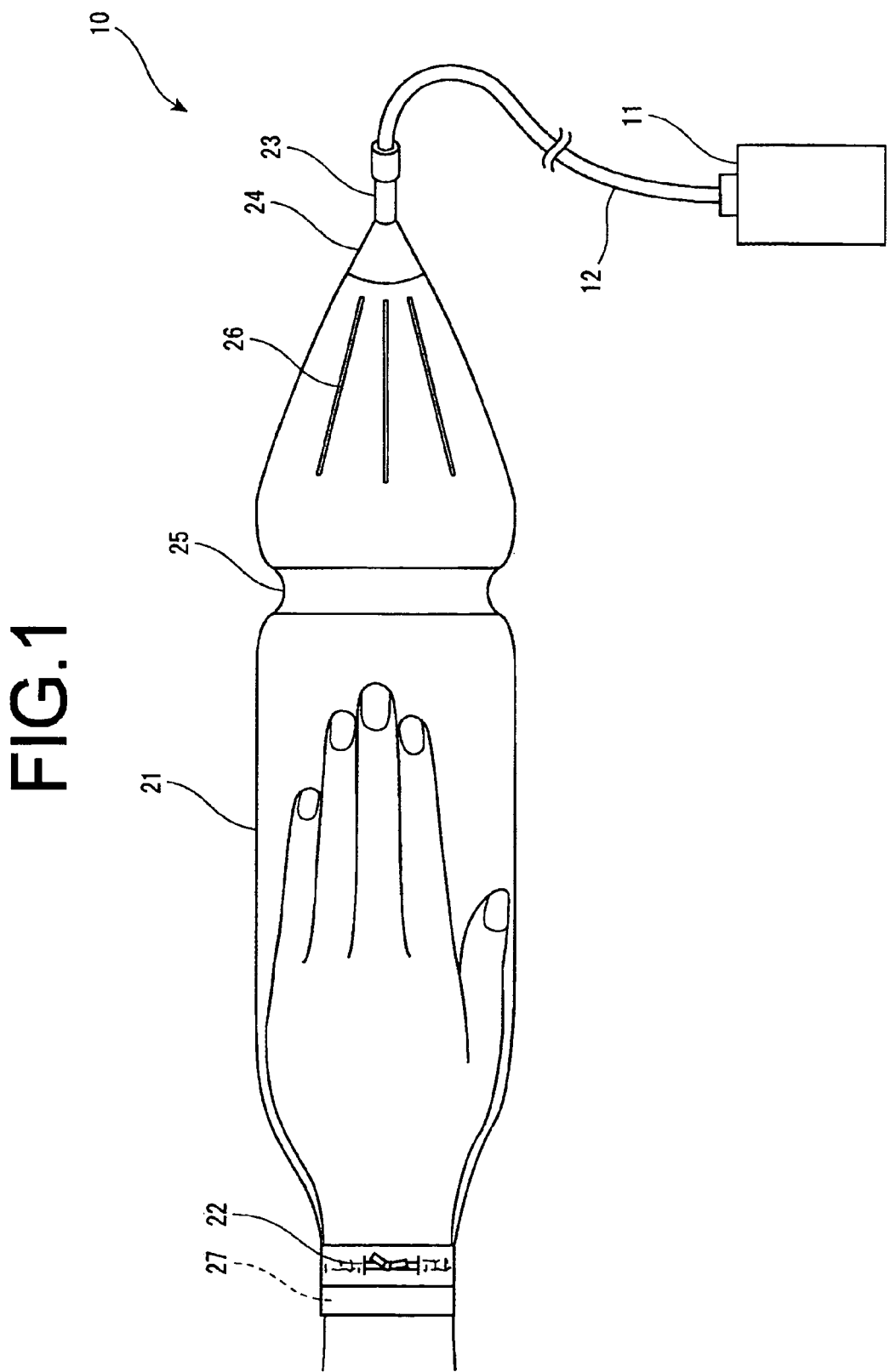
FIG. 1 A generally schematic view of the gas mist pressure bath device depending on a first embodiment of the invention.
Figure 2:
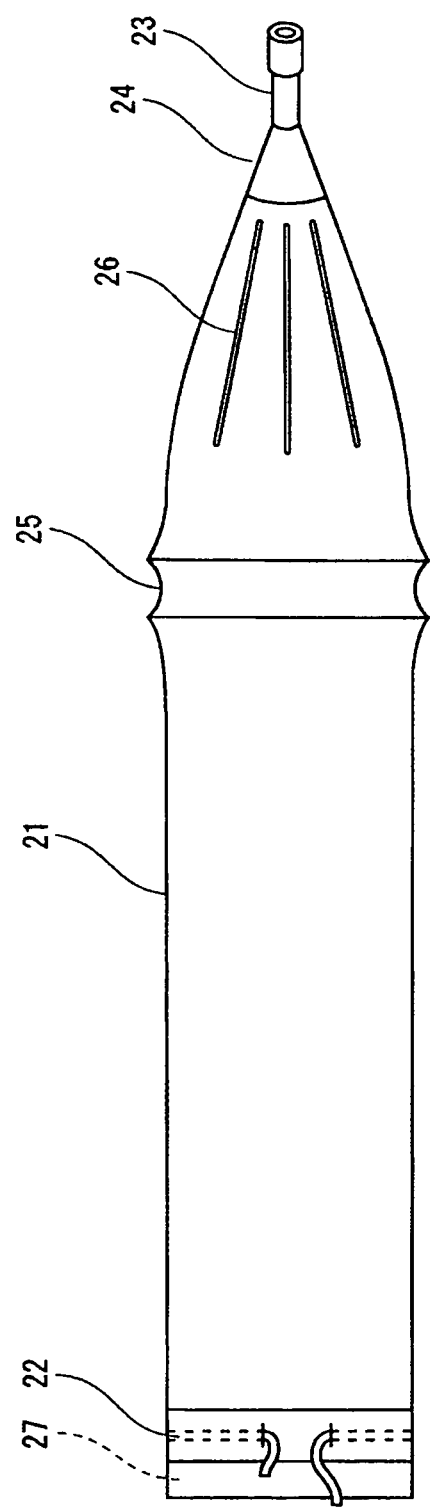
FIG. 2 A perspective view of the living-body cover member in the gas mist pressure bath device depending on the first embodiment of the invention.

FIG. 1 is the generally schematic view of the gas mist pressure bath device depending on the first embodiment of the invention, and FIG. 2 is the perspective view of the living-body cover member in the gas mist pressure bath device.

The gas mist pressure bath device 10 of this embodiment is, as shown in FIG. 1, composed of the gas mist generating device 11 of generating and supplying the gas mist, and a living-body pressure bath cover (living-body cover member) 21 for covering the limited part of the user (herein, for example, a hand of a human living body) and causing the skin or mucous membrane of this part to directly contact and absorb the gas mist.

The gas mist generating device 11 has inside a liquid and a gas supply means such as a gas bomb, otherwise, this is connected to an outside liquid supply means and the gas supply means such as the gas bomb, and generates a mist (gas mist) of having pulverized and liquefied the liquid and gas, and supplies into the living-body pressure bath cover 21. For example, other than a device which is furnished with a fluid nozzle so that high flowing speed of gas from the gas supply means is utilized to pulverize and dissolve the liquid for generating the gas mist, there may be used various kinds of gas mist generating devices, for example, devices of generating the gas mist by jetting gas into the liquid at high pressure. Optimum grain sizes of the mist generated are not more than 10 μm.

In regard to the liquid to be used for generating the gas mist, other than water, ion water or physiological salt solution, it is preferable to use medical liquids useful to users' diseases, symptoms or other conditions, such as anti-allergic agent, anti-inflammatory agent, anti-analgesic and febrile agent, anti-fungus agent, or anti-influenza virus. This liquid is further possible to generate a synergistic effect with a gas physiological action by coupling with single or plurality of menthol having a cooling action; vitamin E accelerating circulation of the blood; vitamin C derivative easily to be absorbed to a skin tissue and having a skin beautifying effect; retinol normalizing a skin heratinizing action and protecting the mucous membrane; anesthetic moderating irritation to the mucous membrane; cyclodextrin removing odor; a complex of photocatalysis and apatite having disinfection and antiphlogistic; hyaluronic acid having excellent water holding capacity and a skin moisture retention effect; coenzyme Q10 activating cells and heightening immunization; a seed oil containing anti-oxidation and much nutrient; or propolith having anti-oxidation, anti-fungus, anti-inflammatory agent, pain-killing, anesthetic, and immunity. Further, high density carbonate spring agent having main components of carbonate and organic acid (as one example of active ingredients, sulfate, carbonate, organic acid or sodium dichloroisocyanurate) may be added.

The generated gas mist is supplied into the living-body pressure bath cover 21 through the gas mist supply pipe 12 connected to the gas mist generating device 11. Inside of the gas mist supply pipe 12, a check valve is provided for checking back flows of the gas mist. In addition, the gas mist supply pipe 12 has a liquid drop removing filter (not shown) for removing excessive liquid drops attached to the inside of the pipe.

Figure 3:
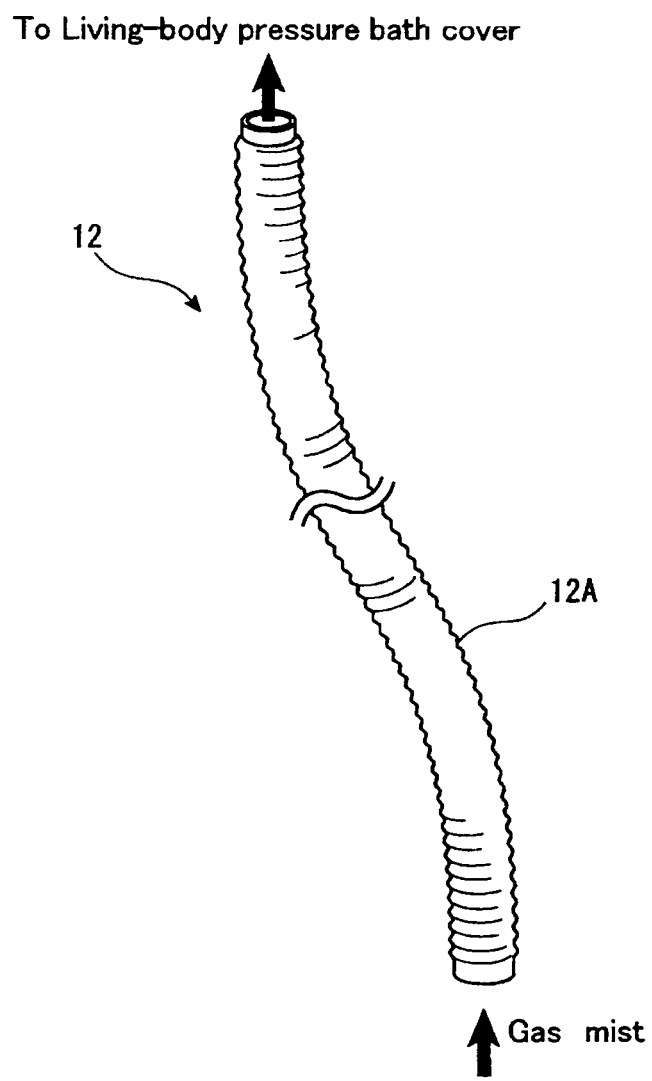
FIG. 3 A typical view showing one example of the gas mist supply pipe used to the gas mist pressure bath device depending on the invention.

Further, as shown in FIG. 3, preferably, the gas mist supply pipe 12 is overall or partially composed of a soft cornice shaped pipe 12A of a large diameter. If composing with such a cornice shaped pipe 12A, the gas mist supply pipe 12A is freely bent and may be expanded so that the user is not restricted in action. Even if the gas mist flowing in the gas mist supply pipe 12 becomes gradually liquefied, the liquid can be removed through concaves and convexes of the cornice.

The living-body pressure bath cover 21 is composed of a substantial bag having a size as large as covering the limited part of the living-body (herein, as the example, the human living body's hand). The substantial bag living-body pressure bath cover 21 is composed of an elastic material, and in regard to the elastic material, when inserting the limited part of the living body into the living body cover, it is shrunk as fitting the skin or mucous membrane and when sealing carbon dioxide, it expands to a certain extent. Since the gas mist is sealed, it is composed of such a material being also non-air permeable and non-moisture permeable material, for example, preferably, silicone rubber, latex rubber or the like.

The living-body pressure bath cover 21 is provided at its opening with a stopper 22 (herein, string) for avoiding leakage of the gas mist. Suitably, the stopper 22 is composed of, for example, a stretchable face fastener, string or rubber. These members may be single or a plurality of combination. Further, for heightening a sealing property, an adhesive part 27 is prepared at a face to be contacted to the user's skin or mucous membrane such as the insides of the stopper 22 or of the living-body pressure bath cover 21. To the side to be contacted by the user's skin or mucous membrane, positioned is an adhesive material to attach the skin or mucous membrane of the living body. Preferably, they are a visco-elastic gel of polyurethane or silicone rubber, and such a material is optimum which is exchangeable each time when viscosity becomes weak.

At a front end opposite to the stopper 22 of the living-body pressure bath cover 21, a gas mist supply mouth 23 is provided, to which a gas mist supply pipe 12 is connected at one end and connected at its other end to the gas mist generating device 11, so that the gas mist is introduced into the living-body pressure bath cover 21. The gas mist supply mouth 23 is inside equipped with a check valve for preventing back flow of the gas. In addition, a sealing part 24 is provided at the front end of the living-body pressure bath cover 21 and at the connecting part of the gas mist supply mouth 23.

Further, the living-body pressure bath cover 21 is formed with a non-stretching part 25 in ring on an outer periphery. The non-stretching part 25 is provided for reinforcing the living-body pressure bath cover 21 and for not increasing capacity of the living-body pressure bath cover 21 by unnecessarily expanding the living-body pressure bath cover 21 when supplying the gas mist thereinto. In addition, the living-body pressure bath cover 21 is formed in vicinity of the front end with ribs 26 for strengthening the living-body pressure bath cover 21.

Explanation will be concretely made to the method of the gas mist pressure bath using the gas mist pressure bath device of the above mentioned structure. At first, the user's limited part to be performed with the gas mist pressure bath is inserted into the living-body pressure bath cover 21. Next, the stopper 22 is attached, and air within the living-body pressure bath cover 21 is extracted as much as possible from the gas mist supply mouth 23. The gas mist supply mouth 23 whose one end is connected to the gas mist generating device 11 is connected at its other end to the gas mist supply mouth 23. In this manner, the inside of the living-body pressure bath cover 21 becomes almost closed. Subsequently, the gas mist is supplied from the gas mist generating device 11. When the gas mist is supplied into the living-body pressure bath cover 21, it expands as a balloon and the internal pressure rises. When the gas mist is at moderate pressure (around 1.02 to 2.5 air pressure) and the gas mist is filled in the living-body pressure bath cover 21 to a degree of enabling to perform the pressure bath, the gas mist from the gas mist generating device 11 is stopped and this condition is maintained to perform the pressure bath. Thereby, the gas mist filled within the living-body pressure bath cover 12 is efficiently absorbed into the skin or mucous membrane.

Omitting illustrations in the above embodiments, the living-body pressure bath cover may be inserted inside with a gas density measuring instrument (carbon dioxide density measuring instrument and oxygen density measuring instrument) or pressure gauge.

Being constructed as above mentioned, according to the gas mist pressure bath device of the invention, since the living-body cover member for carrying out the gas mist pressure bath is composed of an elastic member, the interior of the living-body cover member can be pressurized by only sending the gas mist. Thereby, another pressurizing means is not further requested and the device can be made compact. Since any especial actuation is not necessary, highly effective and easy gas mist pressure bath may be performed by only sending the gas mist into the living-body cover member.

The above explanation has been made to the embodiments of the invention, but the invention is not limited to such embodiments, and so far as not deviating from the subject matter of the invention, various kinds of embodiments are, of course, available.

The present invention relates a gas mist pressure bath device, in which the gas mist is prepared by pulverizing and dissolving carbon dioxide and oxygen or the mixed gas of carbon dioxide and oxygen, and the gas mist is directly contacted to the skin or mucous membrane of the living-body for improving the blood circulation of the living-body, and has an industrial applicability.

DESCRIPTION OF SYMBOLS

10: Gas mist pressure bath device
11: Gas mist generating device
12: Gas mist supply pipe
12A: Cornice shaped pipe
21: Living-body pressure bath cover
22: Stopper
23: Gas mist supply mouth
24: Sealing
25: Non-shrinking part
26: Rib
27: Adhesive part

The invention claimed is:

1. A gas mist pressure bath device for contacting a gas mist at a density of gas in the gas mist not less than a predetermined value with a skin or a mucous membrane of a living-body, comprising:
a gas mist generating unit generating and supplying the gas mist including the gas and a liquid, the gas including oxygen, carbon dioxide or a mixed gas of oxygen and carbon dioxide,
a substantially bag shaped living-body cover member for covering a skin or mucous membrane of the living-body and sealing the gas mist supplied from the gas mist generating unit in the living-body cover member, and a non-stretching ring part disposed on an intermediate part of the living-body cover member and circularly formed at an outer periphery of the living-body cover member to completely surround the same in a ring form to prevent the living-body cover member from expanding more than a predetermined range, wherein the living-body cover member includes a circular cone portion conically expanded from a connecting part which the gas mist generating unit is connected to and a cylindrical portion cylindrically formed from the circular cone portion to an opening portion of the living-body cover member which the living-body is configured to be inserted in;

the non-stretching ring part is disposed at a boundary portion between the circular cone portion and the cylindrical portion;

the circular cone portion includes a plurality of reinforcing members, each reinforcing member is a stick-shaped rib, and the reinforcing members extend in a radial direction from the connecting part to the boundary portion for strengthening the living-body cover member at the circular cone portion, and the gas mist is supplied into the living-body cover member to rise an internal pressure therein, the gas mist is adapted to contact the skin or the mucous membrane of the living-body at a pressure more than the predetermined value, and the gas mist generating unit supplies the gas mist generated by pulverizing the liquid and contacting a pulverized liquid with the gas in the gas mist generating unit.

2. A gas mist pressure bath device as set forth in claim 1, wherein the living-body cover member includes, at the opening portion of the living-body cover member, at least one fastening member fabricated with at least one of a rubber, a string and a face fastener, such that the living-body cover member prevents the gas mist from running away into air atmosphere.

3. A gas mist pressure bath device as set forth in claim 1, wherein at least one adhesive member having viscosity is present on a face of the living-body cover member, the face being adapted to contact the skin or the mucous membrane.

4. A gas mist pressure bath device as set forth in claim 1, wherein the liquid is at least one of water, ionic water, a physiological salt solution, an anti-allergic agent, an anti-inflammatory agent, an anti-febrile, an anti-fungus agent, and anti-influenza virus.

5. A gas mist pressure bath device as set forth in claim 1, wherein the liquid is at least one of water, ionic water, a physiological salt solution, an anti-allergic agent, an anti-inflammatory agent, an anti-febrile, an anti-fungus agent, and anti-influenza virus, which contains at least one of menthol, vitamin E, vitamin C derivative, retinol, anesthetic, cyclodextrin, complex of a photocatalyst and apatite, hyaluronic acid, coenzyme Q10, seed oil, propolith, and high density carbonate spring.

6. A gas mist pressure bath device as set forth in claim 1, wherein at least one particle size of the gas mist supplied from the gas mist generating unit to the living-body cover member is not more than 10 μm.

7. A gas mist pressure bath device as set forth in claim 1, wherein an internal pressure of the living-body cover member is 1.02 to 2.5 air pressure.

8. A gas mist pressure bath device as set forth in claim 1, wherein the living-body cover member has a gas mist supply opening for introducing the gas mist supplied from the gas mist generating unit into the living-body cover member, and the gas mist supply opening has a check valve therein.

9. A gas mist pressure bath device as set forth in claim 1, wherein the gas mist generating unit has a gas mist supply pipe for supplying the gas mist into the living-body cover member, and the gas mist supply pipe has a filter for removing liquid drops attached to the gas mist supply pipe inside.

10. A gas mist pressure bath device as set forth in claim 1, wherein the gas mist generating unit has a gas mist supply pipe for supplying the gas mist into the living-body cover member, and at least a part of the gas mist supply pipe is composed of a cornice shaped pipe.

11. A gas mist pressure bath device as set forth in claim 1, wherein the gas mist generating unit has a gas mist supply pipe for supplying the gas mist into the living-body cover member, and the gas mist supply pipe has a check valve.

12. A gas mist pressure bath device as set forth in claim 1, wherein the living-body cover member is made of an elastic member to expand outwardly to provide the predetermined pressure inside the living-body cover member.

13. A gas mist pressure bath device as set forth in claim 1, wherein the living-body cover member is made of a silicone rubber or a latex rubber to seal the gas mist.

14. A gas mist pressure bath device as set forth in claim 1, wherein the gas mist generating unit has a fluid nozzle that generates pulverized gas mist, each particle of the gas mist including the gas dissolved in the liquid by contacting a flowing gas with the liquid.

15. A gas mist pressure bath device as set forth in claim 2, wherein the living-body cover member has only one non-stretching ring part surrounding the cylindrical portion at the boundary except the at least one fastening member.

* * * * *